United States Patent
Lin

(10) Patent No.: US 11,052,124 B2
(45) Date of Patent: Jul. 6, 2021

(54) METHOD FOR REDUCING FAT ACCUMULATION BY USING EARLY-HARVESTED CITRUS RETICULATA FRUIT EXTRACT

(71) Applicant: TCI CO., LTD., Taipei (TW)

(72) Inventor: Yung-Hsiang Lin, Taipei (TW)

(73) Assignee: TC1 CO., LTD., Taipei (TW)

( * ) Notice: Subject to any disclaimer, the term of this patent is extended or adjusted under 35 U.S.C. 154(b) by 0 days.

(21) Appl. No.: 16/533,865

(22) Filed: Aug. 7, 2019

(65) Prior Publication Data
US 2020/0138893 A1 May 7, 2020

(30) Foreign Application Priority Data
Nov. 5, 2018 (TW) .................. 107139205

(51) Int. Cl.
| | | |
|---|---|---|
| *A61K 36/752* | (2006.01) | |
| *A61K 9/00* | (2006.01) | |
| *A61P 1/00* | (2006.01) | |
| *A61K 31/352* | (2006.01) | |

(52) U.S. Cl.
CPC .......... *A61K 36/752* (2013.01); *A61K 9/0029* (2013.01); *A61K 9/0053* (2013.01); *A61K 31/352* (2013.01); *A61P 1/00* (2018.01); *A61K 2236/35* (2013.01)

(58) Field of Classification Search
None
See application file for complete search history.

(56) References Cited

U.S. PATENT DOCUMENTS

2015/0051272 A1* 2/2015 Pan ........................... A61P 1/16
514/456
2020/0297694 A1* 9/2020 Kato .................... A23K 20/126

FOREIGN PATENT DOCUMENTS

| CN | 100345566 | * 10/2007 |
|---|---|---|
| WO | WO 2016 093613 | * 9/2016 |

OTHER PUBLICATIONS

Putnik, P. et al. Innovative "Green" and Novel Strategies for the Extraction of Bioactive Added Value Compounds from Citrus Wastes—A Review. Molecules 22:1-24, 2017. (Year: 2017).*

* cited by examiner

*Primary Examiner* — Ralph J Gitomer
(74) *Attorney, Agent, or Firm* — Chieh-Mei Wang

(57) ABSTRACT

The present disclosure provides an extract of early-harvested *Citrus reticulata* fruit, and a method for reducing lipid accumulation by using the extract of early-harvested *Citrus reticulata* fruit. The extract of early-harvested *Citrus reticulata* fruit includes tetramethylisoscutellarein.

3 Claims, 3 Drawing Sheets

METHOD FOR REDUCING FAT ACCUMULATION BY USING EARLY-HARVESTED CITRUS RETICULATA FRUIT EXTRACT

CROSS-REFERENCE TO RELATED APPLICATION

This application claims priority of Taiwan patent application No. 107139205, filed on Nov. 5, 2018, the content of which is incorporated herein in its entirety by reference.

BACKGROUND OF THE INVENTION

1. Field of the Invention

The present invention relates to an extract of early-harvested *Citrus reticulata* fruit, and a method for reducing lipid accumulation by using the extract of early-harvested *Citrus reticulata* fruit.

2. The Prior Art

According to statistics, obesity is closely related to cardiovascular diseases, type II diabetes, hyperlipidemia, fatty liver, and mental health. Therefore, obesity is one of the factors that affect human health. Among them, the phenomenon observed in obesity is nothing more than weight gain and/or fat accumulation. When long-term calorie absorption is more than calorie consumption, it will lead to weight gain; and for adults, part of the reason for weight gain is due to increased adipose tissue and increased body fat in the body.

In addition to obesity, the accumulation of triglycerides in the liver is also one of the factors affecting physical health. When the amount of triglycerides in the blood is too high, it can also lead to hyperlipidemia; in addition to causing heart disease, hyperlipidemia is also associated with chronic diseases such as brain infarction, hypertension, diabetes, and kidney diseases.

Modern people are paying more and more attention to health issues. At present, all manufacturers are actively developing medicines and health foods that can reduce fat accumulation. However, most of the conventional pharmaceuticals and health foods are made of chemical components, and long-term use is not only harmful to human health, but these products are often expensive and not affordable to general users.

In order to solve the above problems, those skilled in the art urgently need to develop a novel natural medicament or food product having the effect of reducing fat accumulation for the benefit of a large group of people in need thereof.

SUMMARY OF THE INVENTION

A primary objective of the present invention is to provide an extract of early-harvested *Citrus reticulata* fruit, which is prepared by a process comprising the steps of: (a) extracting the early-harvested *Citrus reticulata* fruit with an extraction solvent to obtain a crude extract; (b) subjecting a partitioning treatment to the crude extract using a solvent mixture of ethyl acetate and water to form an ethyl acetate layer and an aqueous layer; and (c) collecting the ethyl acetate layer, followed by removing the ethyl acetate, thereby obtaining the extract of early-harvested *Citrus reticulata* fruit.

According to an embodiment of the present invention, the extracting is at an extraction temperature ranging from 70° C. to 100° C.

According to an embodiment of the present invention, a volume ratio of the extraction solvent and the early-harvested *Citrus reticulata* fruit is 1:1 to 3:1.

According to an embodiment of the present invention, in step (b), a volume ratio of the ethyl acetate and the water in the solvent mixture is 1:1.

According to an embodiment of the present invention, the extraction solvent is water, an alcohol, an aqueous alcohol, or a combination thereof.

According to an embodiment of the present invention, the extract of early-harvested *Citrus reticulata* fruit comprises tetraethylisoscutellarein, wherein the tetramethylisoscutellarein has a chemical formula (I):

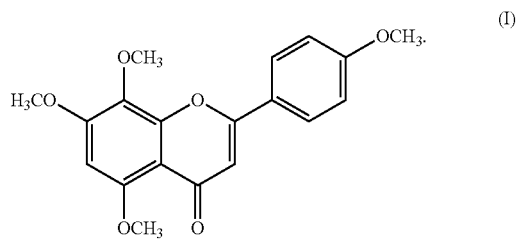 [SMILES: COc1ccc(-c2cc(=O)c3c(OC)cc(OC)c(OC)c3o2)cc1]

According to an embodiment of the present invention, the tetramethylisoscutellarein is purified by a column chromatography.

Another objective of the present invention is to provide a method for reducing fat accumulation, comprising administering to a subject in need thereof a composition comprising an effective amount of the above-mentioned extract of early-harvested *Citrus reticulata* fruit.

Another objective of the present invention is to provide a method for reducing fat accumulation, comprising administering to a subject in need thereof a composition comprising an effective amount of tetramethylisoscutellarein, wherein the composition is in a form of a pharmaceutical composition or a food product, and the tetramethylisoscutellarein has a chemical formula (I):

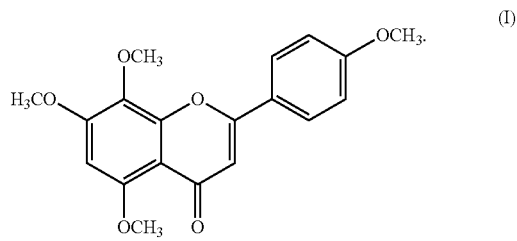 [SMILES: COc1ccc(-c2cc(=O)c3c(OC)cc(OC)c(OC)c3o2)cc1]

According to an embodiment of the present invention, the pharmaceutical composition comprises a pharmaceutically acceptable carrier.

According to an embodiment of the present invention, the pharmaceutical composition is in a dosage form for parenteral administration.

According to an embodiment of the present invention, the pharmaceutical composition is in a dosage form for oral administration.

In summary, the extract of early-harvested *Citrus reticulata* fruit has the effect on inhibiting fat accumulation and thereby achieving the effect of reducing fat.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
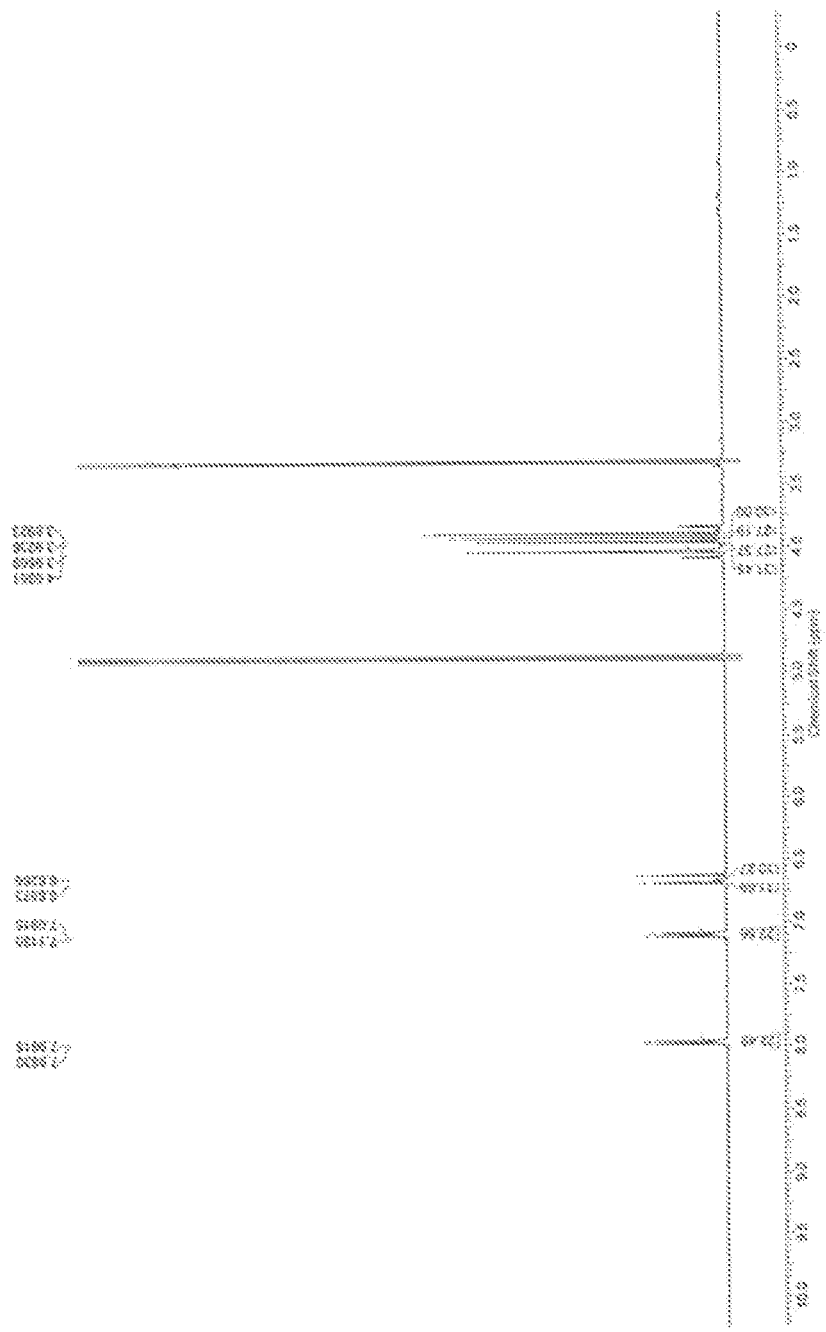
FIG. 1 is a $^1$H nuclear magnetic resonance spectrum of the compound TCI-CR-03.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Statistical analysis was performed using Excel. Data are expressed as mean±standard deviation (SD), and the difference between each group is analyzed by the Student's t-test.

According to the present invention, *Citrus reticulata* is a broad-skin *Citrus* in the family Rutaceae and the genus *Citrus*. The early-harvested fruit has a thick outer skin and contains a sacral flap composed of juice and seeds. The production areas are mainly distributed in China, Spain, Brazil and Japan. Vitamin A in *Citrus reticulata* enhances the vision of human body in dark environments and treats night blindness. *Citrus reticulata* should not be eaten too much. If *Citrus reticulate* is eaten too much, caroteneemia will be got easily, and the skin is dark yellow, like jaundice.

As used herein, the term "early-harvested *Citrus reticulata* fruit" refers to a *Citrus reticulata* fruit having a diameter of 3 to 5 cm, 60 to 90 days after flowering of the *Citrus reticulata* flower.

According to the present invention, the extract of early-harvested *Citrus reticulata* fruit can be prepared using fresh early-harvested *Citrus reticulata* fruit, or early-harvested *Citrus reticulata* fruit which is processed in advance selected from the group consisting of: drying treatment, grinding treatment, chopping treatment, and combinations thereof.

As used herein, the term "tetramethylisoscutellarein" or "the compound TCI-CR-03" also known as 5784'-tetramethoxyflavone, is a member of the compound 8-o-methylated flavonoids. Tetramethylisoscutellarein has the following chemical formula (I):

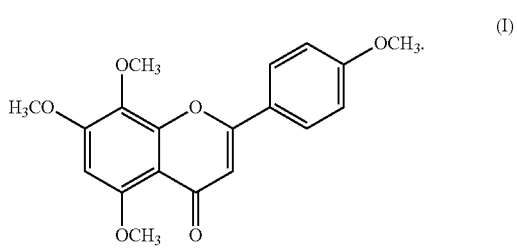 [SMILES: COc1ccc(-c2cc(=O)c3c(OC)cc(OC)c(OC)c3o2)cc1]

According to the present invention, the pharmaceutical composition can be manufactured to a form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intramuscular injection and intravenous injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, disintegrating agent, dispersing agent, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

According to the present invention, the food product can be used as a food additive, added by the conventional method in the preparation of the raw material, or added during the preparation of food, and prepared with any edible material into food products for human and non-human animals.

According to the present invention, types of food products include, but not limited to, beverages, fermented foods, bakery products, health foods, and dietary supplements.

Example 1

Preparation and Purification of Extract of Early-Harvested *Citrus reticulata* Fruit and its Compound 1.1 Preparation of Extract of Early-Harvested *Citrus reticulata* Fruit First, the early-harvested *Citrus reticulata* fruit was pulverized to a size of about 1 to 2 cm, and then the pulverized early-harvested *Citrus reticulata* fruit was extracted by using water, an alcohol, an aqueous alcohol or a combination thereof as an extraction solvent, wherein the extracting is at an extraction temperature ranging from 70° C. to 100° C., and the volume ratio of the extraction solvent and the early-harvested *Citrus reticulata* fruit is 1:1 to 3:1. Next, the obtained crude extract was centrifuged, and the supernatant after centrifugation was taken and filtered to obtain a filtrate. Thereafter, the filtrate was concentrated under reduced pressure at 45° C. to 70° C. to obtain a concentrated product (hereinafter referred to as the original extract of early-harvested *Citrus reticulata* fruit). 2 L of the original extract of early-harvested *Citrus reticulata* fruit was taken and a partitioning treatment in liquid phase was subjected in an equal ratio (1:1 (v/v)) of ethyl acetate to water for 3 times to form an ethyl acetate layer and an aqueous layer (hereinafter referred to as an aqueous layer extract of early-harvested *Citrus reticulata* fruit). Thereafter, the ethyl acetate layer was collected, and then ethyl acetate was removed, followed by concentration under reduced pressure and drying, thereby obtaining the extract of early-harvested *Citrus reticulata* fruit. In addition, an n-butanol layer extract of early-harvested *Citrus reticulata* fruit was also prepared with a preparation process similar with that of the extract of early-harvested *Citrus reticulata* fruit, except that ethyl acetate is substituted with n-butanol.

1.2 Purification of Tetramethylisoscutellarein

First, according to the bioassay guided fractionation method, 5.4 g of the extract of early-harvested *Citrus reticulata* fruit was mixed with a mixing solvent system of dichloromethane and methanol (15:1), and a silica gel column chromatography (filling materials include Sephadex LH-20 (Amersham Biosciences), Diaion HP-20 (Mitsubishi Chemical), Merck Kieselgel 60 (40-63 µm, Art. 9385), and Merck LiChroprep® RP-18 (40-63 µm, Art. 0250)) was performed to isolate 10 fractions (F-1 to F-10). Next, the second fraction (F-2) was mixed with a mixing solvent system of water and methanol (1:1), and C18 column chromatography was performed to isolate five fractions (F-2-1 to F-2-5). Thereafter, the fraction F-2-4 was mixed with a mixing solvent system of water and methanol (1.5:1), and C18 column chromatography was performed to obtain 5.3 mg of the compound TCI-CR-03.

The compound TCI-CR-03 is a pale yellow oil and subjected to $^1$H nuclear magnetic resonance spectrometer ($^1$H NMR) analysis (1D and 2D spectra using 400 MHz Varian 400 FT-NMR: δ represents the chemical shift in ppm; TMS (tetramethylsilane; δ=0) is used as the internal standard; coupling constant (J) is in Hz, and s represents singlet, d represents doublet, t represents triplet, q represents quartet, p represents quintet, m represents multiplet, and brs represents broad singlet). The result is shown in FIG. 1. FIG. 1 is a $^1$H nuclear magnetic resonance spectrum of the compound TCI-CR-03. As shown in FIG. 1, there are two sets of aromatic ring regions that couple protons $\delta_H$ 7.10 (2H, d, J=84 Hz), $\delta_H$ 7.99 (1H, d, J=8.4 Hz), and two singlets proton signals at $\delta_H$ 6.6 (1H, s), $\delta_H$ 6.7 (1H, s), and the signals of four methoxy groups were found to be at $\delta_H$ 3.89, $\delta_H$ 3.92, $\delta_H$ 3.96, $\delta_H$ 4.04, respectively. Based on the comparison of the above spectral information with the literature, it was confirmed that the compound TCI-CR-03 is tetramethylisoscutellarein.

Example 2

Evaluation of Effect of Early-Harvested *Citrus Reticulata* Fruit and its Compound on Reducing Fat Accumulation 2.1 Evaluation of Effect of Early-Harvested *Citrus reticulata* Fruit on Reducing Fat Accumulation First, 8×10$^4$ mouse bone marrow stromal cell OP9 (ATCC® CRL-2749™) was seeded with 500 µL of pre-adipocyte expansion medium (supplemented with 90% minimum essential medium alpha medium (Gibco), 20% fetal bovine serum (Gibco) and 1% penicillin/streptomycin (Gibco)) in a 24-well plate, and incubated at 37° C. for 7 days. Fresh differentiation medium (supplemented with 90% minimum essential medium alpha medium, 20% fetal bovine serum, and 1% penicillin/streptomycin) was replaced every three days. After 7 days, lipid droplet formation was observed using microscopy (ZEISS) to make sure the cells are fully differentiated.

Thereafter, five groups of OP9 cells (i.e. an experimental group, three comparative groups (comparative group 1 to comparative group 3) and a control group) were prepared. 1 mg/mL original extract of early-harvested (*Citrus reticulata* fruit was added to the cells in the comparative group 1, 1 mg/mL n-butanol layer extract of early-harvested *Citrus reticulata* fruit was added to the cells in the comparative group 2, 1 mg/mL aqueous layer extract of early-harvested *Citrus reticulata* fruit was added to the cells in the comparative group 3, 1 mg/mL extract of early-harvested *Citrus reticulata* fruit was added to the cells in the experimental group, and the cells in the control group were left without any treatment. The cells in each group were incubated for another 7-10 days and the medium was changed every 3 days.

Medium was gently removed and each well was rinsed twice with 1.0 mL of PBS. 1.0 mL of 10% formaldehyde (ECHO) was added to fix the cells and the cells were incubated for 30 minutes at room temperature (RT). The formaldehyde was removed and each well was gently rinsed twice with 1.0 mL of PBS. 1.0 mL of 60% isopropanol (ECHO) was added to each well and incubation for 1 minute. After removing isopropanol, 1.0 mL of oil-red O working solution (60% stock solution of oil-red O staining reagent (Sigma; stock concentration: 3 mg/mL in 100% isopropanol) prepared with ddH$_2$O) was added and incubated 1 hour at RT. Oil-red O working solution was removed and quickly destained with 1.0 mL of 60% isopropanol for 5 sec, followed by using microscopy to take pictures.

The oil droplet was dissolved using 100% isopropanol, and the plate was put on shaker and incubation for 10 min. A volume of 100 µL was taken to 96-well plate for measuring the O.D ratio (510 nm) with the ELISA reader (BioTek).

The statistical significance of the differences between each group was determined by Student's t-test in Microsoft Excel. The result is shown in FIG. 2.

Figure 2:
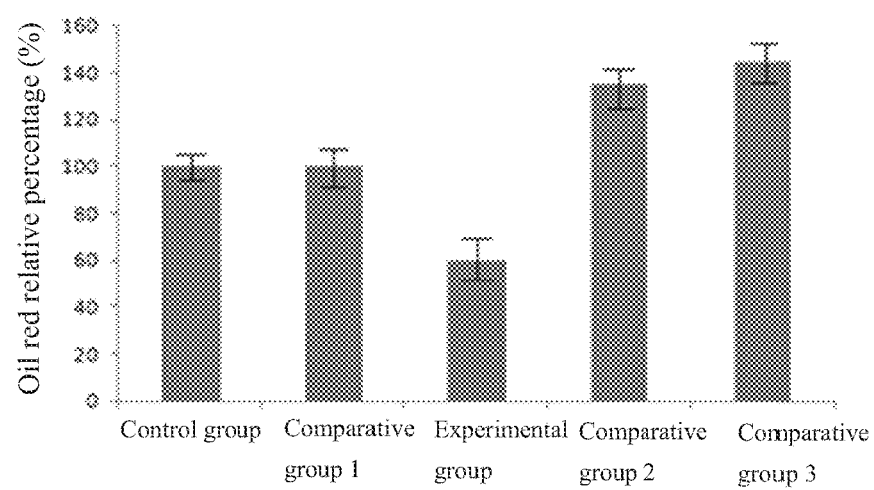
FIG. 2 is a data diagram showing the effect of the extract of early-harvested *Citrus reticulata* fruit of the present invention on reducing fat accumulation.

FIG. 2 is a data diagram showing the effect of the extract of early-harvested *Citrus reticulata* fruit of the present invention on reducing fat accumulation. As shown in FIG. 2, compared with the control group and the comparative groups 1 to 3, the oil red relative percentage of the experimental group was reduced. The result of this example shows that the extract of early-harvested *Citrus reticulata* fruit of the present invention has the effect on reducing fat accumulation.

2.2 Evaluation of Effect of Tetramethylisoscutellarein on Reducing Fat Accumulation First, 8×10$^4$ mouse bone marrow stromal cell OP9 (ATCC® CRL-2749™) was seeded with 500 µL of pre-adipocyte expansion medium (supplemented with 90% minimum essential medium alpha medium, 20% fetal bovine serum and 1% penicillin/streptomycin) in a 24-well plate, and incubated at 37° C. for 7 days. Fresh differentiation medium (supplemented with 90% minimum essential medium alpha medium, 20% fetal bovine serum, and 1% penicillin/streptomycin) was replaced every three days. After 7 days, lipid droplet formation was observed using microscopy (ZEISS) to make sure the cells are fully differentiated.

Thereafter, two groups of OP9 cells (i.e. an experimental group and a control group) were prepared. 10 µg/mL tetramethylisoscutellarein was added to the cells in the experimental group, and the cells in the control group were left without any treatment. The cells in each group were incubated for another 7-10 days and the medium was changed every 3 days.

Medium was gently removed and each well was rinsed twice with 1.0 mL of PBS. 1.0 mL of 10% formaldehyde was added to fix the cells and the cells were incubated for 30 minutes at room temperature (RT). The formaldehyde was removed and each well was gently rinsed twice with 1.0 mL of PBS. 1.0 ml of 60% isopropanol was added to each well and incubation for 1 minute. After removing isopropanol, 1.0 mL of oil-red O working solution (6)% stock solution of oil-red O staining reagent (Sigma; stock concentration: 3 mg/mL in 100% isopropanol) prepared with ddH$_2$O) was added and incubated 1 hour at RT. Oil-red O working solution was removed and quickly destained with 1.0 mL of 60% isopropanol for 5 sec, followed by using microscopy to take pictures.

The oil droplet was dissolved using 100% isopropanol, and the plate was put on shaker and incubation for 10 min. A volume of 100 µL was taken to 96-well plate for measuring the O.D ratio (510 nm) with the ELISA reader.

The statistical significance of the differences between each group was determined by Student's t-test in Microsoft Excel. The result is shown in FIG. 3.

Figure 3:
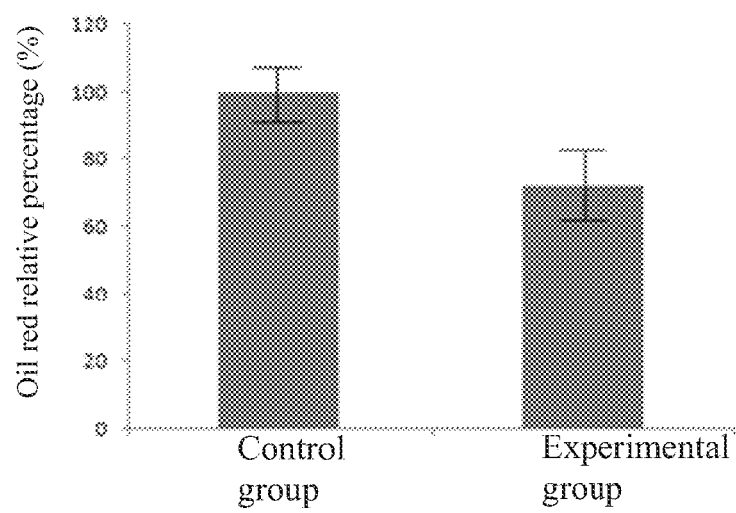
FIG. 3 is a data diagram showing the effect of tetramethylisoscutellarein (i.e. the compound TCI-CR-03) on reducing fat accumulation.

FIG. 3 is a data diagram showing the effect of tetramethylisoscutellarein on reducing fat accumulation. As shown in FIG. 3, compared with the control group, the oil red relative percentage of the experimental group was reduced (28% lower than the control group). The result of this example shows that tetramethylisoscutellarein isolated from the extract of early-harvested *Citrus reticulata* fruit of the present invention also has the effect on reducing fat accumulation.

In summary, the extract of early-harvested *Citrus reticulata* fruit and tetramethylisoscutellarein isolated from the extract of early-harvested *Citrus reticulata* fruit have the effect on inhibiting fat accumulation and thereby achieving the effect of reducing fat.

Although the present invention has been described with reference to the preferred embodiments, it will be apparent to those skilled in the art that a variety of modifications and changes in form and detail may be made without departing from the scope of the present invention defined by the appended claims.

The invention claimed is:

1. A method for reducing fat accumulation, comprising administering to a subject in need thereof a composition comprising an effective amount of an extract of early-harvested *Citrus reticulata* fruit which is prepared by a process comprising the steps of:
   (a) extracting the early-harvested *Citrus reticulata* fruit with an extraction solvent to obtain a crude extract, wherein the early-harvested *Citrus reticulata* fruit is a *Citrus reticulata* fruit harvested 60 to 90 days after flowering of a *Citrus reticulata* flower, and the extraction solvent is water;
   (b) subjecting a partitioning treatment to the crude extract using a solvent mixture of ethyl acetate and water to form an ethyl acetate layer and an aqueous layer; and
   (c) collecting the ethyl acetate layer, followed by removing the ethyl acetate, thereby obtaining the extract of early-harvested *Citrus reticulata* fruit.

2. The method of claim 1, wherein the extraction temperature for the early-harvested *Citrus reticulata* fruit ranges from 70° C. to 100° C.

3. The method of claim 1, wherein a volume ratio of the extraction solvent and the early-harvested *Citrus reticulata* fruit is 1:1 to 3:1.

* * * * *